| United States Patent [19] | [11] | 4,055,414 |
|---|---|---|
| Chupp | [45] | Oct. 25, 1977 |

[54] HERBICIDAL COMPOSITION AND METHOD OF USE

[75] Inventor: John P. Chupp, Kirkwood, Mo.

[73] Assignee: Monsanto Company, St. Louis, Mo.

[21] Appl. No.: 665,972

[22] Filed: Mar. 11, 1976

[51] Int. Cl.$^2$ .................... A01N 9/20; C07C 101/447
[52] U.S. Cl. ........................................ 71/111; 560/39; 560/41; 560/29; 560/30; 560/31; 560/32; 560/22; 560/21; 560/34; 260/404.5
[58] Field of Search .......... 71/111; 260/471 R, 471 A

[56] References Cited

U.S. PATENT DOCUMENTS

| 3,769,301 | 10/1973 | Olin | 71/118 |
|---|---|---|---|
| 3,901,685 | 8/1975 | Ratts | 71/118 |
| 3,907,544 | 9/1975 | Olin | 71/118 |
| 3,993,679 | 11/1976 | Hall et al. | 260/471 A X |
| 4,018,813 | 4/1977 | Gaughan | 260/471 A |

*Primary Examiner*—Joseph Paul Brust
*Attorney, Agent, or Firm*—William I. Andress; Donald W. Peterson

[57] ABSTRACT

The disclosure herein relates to 2-halo-N-(N$^1$-hydrocarbyloxyoxalyl-N$^1$-acylaminomethyl)-2',6'-dialkylacetanilides, to a process for preparing these compounds, herbicidal compositions containing same and method of use to selectively control undesired vegetation in agricultural crops, e.g., monocotyledons such as wheat, sorghum and rice and dicotyledons such as sugarbeets and soybeans.

16 Claims, No Drawings

HERBICIDAL COMPOSITION AND METHOD OF USE

BACKGROUND OF THE INVENTION

The invention herein pertains to the field of herbicidal compounds, processes and compositions. In more particular, the herbicidal compositions herein have particular application in the control of undesired plants associated with monocotyledons such as wheat, sorghum and rice and dicotyledons such as sugarbeets and soybeans. Additional aspects of this invention pertain to a process for the preparation of the novel compounds herein.

DESCRIPTION OF THE PRIOR ART

It is known in the prior art to prepare 2-haloacetanilides having a variety of substituents on the phenyl ring and on the anilide nitrogen atom. It is also known that the substituent on the anilide nitrogen atom can be amido or acylamidoalkylene groups.

Illustrative of the prior art compounds most closely related in structure to the invention compounds are the compounds disclosed in U.S. Pat. Nos. 3,830,841 and 3,901,685 (both to K. W. Ratts), 3,769,301 and 3,907,544 (a division of the U.S. Pat. No. 3,769,301 patent; both to J. F. Olin), all of these patents are assigned to the assignee herein. The U.S. Pat. Nos. 3,769,301 and 3,830,841 disclose substituted amidoalkyl- b 2-haloacetanilides which may have a variety of substituents on the acyl and phenyl moieties of the compound. A characteristic feature of these compounds is the presence of a hydrogen atom on the nitrogen atom of the acylamidoalkyl group.

Most closely pertinent to the compounds of this invention are those of the above-mentioned U.S. Pat. Nos. 3,769,301 and 3,907,544 to Olin. In these patents are disclosed compounds which may have an N-substituted acylamidomethyl group containing a substituted oxalyl attached thereto. In the generic formula of these patents the substituent on the oxalyl moiety may be an alkyl, alkenyl, alkynyl, aryl or alkaryl group. However, none of the prior art references disclose compounds having an $N^1$-hydrocarbyloxyoxalyl-$N^1$-acylaminomethyl radical attached to the anilide nitrogen atom.

The processes disclosed in the above patents for preparing the 2-haloacetanilides disclosed therein include: (1) reacting an 2-halo-N-(halo-substituted methyl or ethyl) acetanilide with a nitrile or an inorganic cyanide under acid conditions; (2) reacting a nitrile with an 2-halo-o,o-disubstituted N-alkoxymethyl acetanilide of the type disclosed in U.S. Pat. No. 3,442,945; (3) reacting a substituted phenylazomethine with a substituted amide or imide to form the corresponding N-(anilinomethyl) amide or imide, which is then haloacetylated to provide the corresponding appropriately substituted 2-haloacetanilide.

The herbicidal compositions and method of use described in said prior art patents relate to use of the novel compounds disclosed therein to control undesired vegetation in crops.

SUMMARY OF THE INVENTION

The present invention relates to: (1) novel 2-halo-N-($N^1$-hydrocarbyloxyoxalyl-N-acylaminomethyl)-2',6'-dialkylacetanilides; (2) a novel process for preparing these compounds; (3) herbicidal compositions containing said compounds, and (4) herbicidal method of use, particularly to control noxious weeds in sugarbeets, soybeans, wheat, sorghum and rice.

In more particular, the compounds of this invention are those having the formula

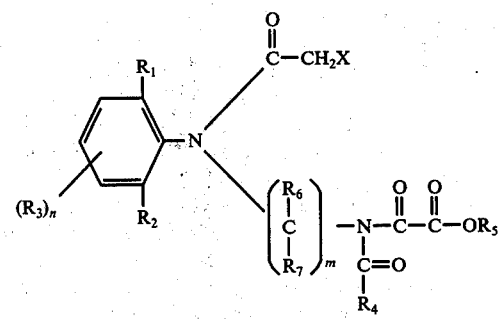

wherein
$R_1$ and $R_2$ are independently hydrogen, halogen, $C_{1-10}$ alkyl or alkoxy and may be the same or different;

$R_3$ is halogen, $C_{1-10}$ alkyl or alkoxy or $NO_2$ and when n is 2 or 3 these groups may be the same or different;

$R_4$ is hydrogen, alkyl, alkenyl, alkynyl, alkoxy, polyalkoxy, alkoxyalkyl, polyalkoxyalkyl, haloalkyl, hydroxyalkyl, haloalkenyl, oxoalkyl, alkenyloxyalkyl, each of a maximum of 18 carbon atoms; $C_{3-6}$ cycloalkyl; aryl, alkaryl, aralkyl, aryloxy, or aryloxyalkyl, each of which may be substituted with halogen, alkyl and/or nitro groups and having at least 6 and not more than 24 carbon atoms; amino or mono- and dialkylamino, monoarylamino, mono(haloaryl)amino, mono(trifluoromethylaryl)amino, and alkylalkoxyamino having a maximum of 10 carbon atoms;

$R_5$ is a hydrocarbyl group selected from the group consisting of alkyl, alkenyl, aryl, aralkyl or alkaryl having a maximum of 18 carbon atoms;

$R_6$ and $R_7$ are hydrogen or $C_{1-4}$ alkyl and may be the same or different. When m is greater than 1, numbering of the resultant alkylene group begins from the anilino nitrogen atom.

X is chlorine, bromine or iodine,
m is an integer of 1 to 4 inclusive and n is an integer of 0 to 3 inclusive.

Unless otherwise indicated, "alkyl" and "alkoxy" are used generically to include primary, secondary, and tertiary groups.

Representative compounds of the present invention include those in which the groups of the above formula have the following identities:

$R_1$ and $R_2$ — hydrogen, chlorine, bromine, iodine, fluorine, methyl, ethyl, propyl, isopropyl, n-butyl, primary isobutyl, secondary isobutyl, tertiary butyl, n-amyl, branch chain amyls, the normal and branched hexyls, heptyls, octyls, nonyls, and decyls, methoxy, ethoxy, propoxy, butoxy, pentyloxy, heptyloxy, nonyloxy;

$R_3$ — hydrogen, chlorine, bromine, iodine, fluorine, nitro and the alkyl and alkoxy groups of $R_1$ and $R_2$;

$R_4$ — hydrogen, methyl, ethyl, propyl, isopropyl, n-butyl, isobutyl, tertiary butyl, the normal and branched amyls, hexyls, heptyls, octyls, nonyls, decyls, dodecyls, tetradecyls, hexadecyls and octadecyls; chloromethyl, bromopropyl, iodobutyl, fluorohexyl, hydroxyethyl, dihydroxypropyl; the alkoxy, alkenyl, oxoalkyl, alkoxyalkyl and alkynyl groups corresponding to the above-enumerated alkyl groups; phenyl, tolyl, naphthyl, phenoxy, benzyl, phenoxyalkyl, each of which may be substituted with one or more alkyl, halo and/or nitro groups; and the like.

$R_5$ — the alkyl, alkenyl, alkynyl, aryl, aralkyl and alkaryl groups of $R_4$.

$R_6$ and $R_7$— hydrogen, methyl, ethyl and the various propyl and butyl isomers.

The preferred compounds of the present invention are those in which $m$ is 1; $n$ is 0 or 1; X is chlorine, bromine or iodine; $R_6$ and $R_7$ are hydrogen and the remaining R's are $C_{1-10}$ alkyl, preferably the $C_{1-5}$ alkyls, or at least one of $R_1$ and $R_3$ are halogen when $R_2$ is lower alkyl, preferably t-alkyl (preferably t-butyl).

The specific compound of preference is 2-chloro-N-($N^1$-ethoxyoxalyl acetamidomethyl)-2',6'-diethylacetanilide.

The novel process according to this invention appears to be a general reaction involving the oxalylation of secondary amides with hydrocarbyloxyoxalyl halides, preferably alkoxyoxalyl chlorides, e.g., ethoxyoxalyl. The preferred compounds of this invention are produced by reaction appropriately-substituted a-haloacetanilides of the type disclosed in the above-mentioned U.S. Pat. Nos. 3,830,841 and 3,901,685 to K. W. Ratts with the appropriate hydrocarbyloxyoxalyl chloride as further detailed below.

Another aspect of this invention concerns the use of the invention compounds as the active ingredient in herbicidal compositions. These compositions have particular utility in selectively controlling weeds in sugarbeets, soybeans, wheat, sorghum and rice.

Still another aspect of this invention concerns the method of using the herbicidal compositions herein as selective herbicides by applying them to the locus of undesirable plants to be controlled and desirable plants to be protected.

The invention will be more clearly understood by reference to the following detailed description of specific examples thereof. In these examples and throughout the specification, all proportions are expressed in part by weight unless otherwise indicated.

DETAILED DESCRIPTION OF THE INVENTION

Example

This example describes the preparation of 2-chloro-N-($N^1$-ethoxyoxalyl acetamidomethyl)-2',6'-diethylacetanilide.

N-acetamidomethyl-2', 6'-diethyl-2 -chloroacetanilide, 29.6 g (0.1 mol), and an equimolar amount, 13.6 g (0.1 mol), of ethoxyoxalyl chloride were placed in 300 ml toluene and the mixture heated at reflux temperature for 3 hours. The mixture was then cooled and toluene removed under vacuum. The residual solid was then recrystallized from methanol to give 27.5 g (69% yield) of the title compound of this example, m.p. 80°–81° C. This compound had the following elemental analysis:

| Anal. | Cal'd | ($C_{19}H_{25}ClN_2O_5$) | Found |
|---|---|---|---|
| C | 57.50 | | 57.48 |
| H | 8.93 | | 8.99 |
| N | 7.06 | | 7.06 |

EXAMPLES 2 to 63

The compounds in the following examples may also be prepared by substantial repetition of the general procedures set forth in the foregoing examples, modified as to reaction temperatures, times, solvents, etc., to account for the nature of the particular reactants, as will be apparent to those skilled in the art. In the examples, the individual compounds are those whose members are identified by the general formula

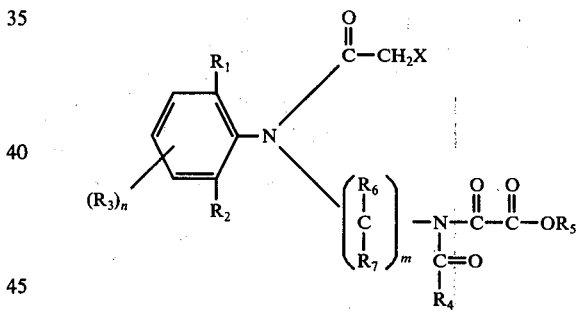

| Example | $R_1$ | $R_2$ | $R_3$ | $R_4$ | $R_5$ | $R_6$ | $R_7$ | X | m | n |
|---|---|---|---|---|---|---|---|---|---|---|
| 2 | ethyl | ethyl | H | methyl | ethyl | H | H | Cl | 2 | 0 |
| 3 | ethyl | ethyl | H | 2,6-dichlorophenyl | ethyl | H | H | Cl | 1 | 0 |
| 4 | ethyl | ethyl | H | 3-butenyl | ethyl | H | H | Cl | 1 | 0 |
| 5 | ethyl | ethyl | H | H | ethyl | H | H | Cl | 1 | 0 |
| 6 | methyl | t-butyl | H | 3-chloro-2-methylpropyl | ethyl | H | H | Cl | 1 | 0 |
| 7 | methyl | t-butyl | H | methyl | ethyl | H | H | Cl | 1 | 0 |
| 8 | methyl | methyl | H | cyclopropyl | ethyl | H | H | Cl | 1 | 0 |
| 9 | methyl | methyl | H | cinnamyl | ethyl | H | H | Cl | 1 | 0 |
| 10 | isopropyl | isopropyl | H | propyl | methyl | H | H | Cl | 1 | 0 |
| 11 | methyl | methyl | 4'-methyl | methyl | methyl | H | H | Cl | 1 | 1 |
| 12 | ethyl | ethyl | 4'-methyl | 2-chloromethyl | methyl | H | H | I | 1 | 1 |
| 13 | ethyl | ethyl | H | 3-ethoxypropyl | n-propyl | H | H | Cl | 1 | 0 |
| 14 | ethyl | ethyl | H | 2-chloromethyl | n-butyl | H | H | Cl | 1 | 0 |
| 15 | ethyl | ethyl | H | i-propyl | i-butyl | H | H | Cl | 1 | 0 |
| 16 | ethyl | ethyl | H | dodecyl | ethyl | H | H | Br | 1 | 0 |
| 17 | ethyl | ethyl | H | 2-chloroethyl | ethyl | H | H | Br | 1 | 0 |
| 18 | ethyl | ethyl | H | ethyl | ethyl | H | H | Cl | 1 | 0 |
| 19 | ethyl | ethyl | H | propyl | ethyl | H | H | Cl | 1 | 0 |
| 20 | ethyl | ethyl | H | carbamoyl | ethyl | H | H | Cl | 1 | 0 |
| 21 | ethyl | ethyl | H | amino | ethyl | H | H | Cl | 1 | 0 |

-continued

| Example | $R_1$ | $R_2$ | $R_3$ | $R_4$ | $R_5$ | $R_6$ | $R_7$ | X | m | n |
|---|---|---|---|---|---|---|---|---|---|---|
| 22 | ethyl | ethyl | H | phenyl | ethyl | H | H | Cl | 1 | 0 |
| 23 | ethyl | ethyl | H | benzyl | ethyl | H | H | Cl | 1 | 0 |
| 24 | ethyl | ethyl | H | methyl | ethyl | H | H | Cl | 1 | 0 |
| 25 | ethyl | ethyl | H | lauryl | ethyl | H | H | Cl | 1 | 0 |
| 26 | methyl | methyl | H | methyl | methyl | H | H | Br | 1 | 0 |
| 27 | t-butyl | H | H | pentyl | t-butyl | H | H | Cl | 1 | 0 |
| 28 | methyl | ethyl | H | methyl | propyl | H | H | Cl | 1 | 0 |
| 29 | ethyl | ethyl | H | 2,3-dichloro-ethyl | methyl | H | H | Cl | 1 | 0 |
| 30 | ethyl | ethyl | H | cyclopropyl | hexyl | H | H | Cl | 1 | 0 |
| 31 | ethyl | ethyl | H | 2-methoxy-ethyl | allyl | H | H | Cl | 1 | 0 |
| 32 | ethyl | t-butyl | H | $CH_3$ | sec-butyl | H | H | Br | 1 | 0 |
| 33 | ethyl | ethyl | H | $CH_3$ | ethyl | H | H | Cl | 1 | 0 |
| 34 | ethyl | ethyl | H | 2,6-dichloro-phenyl | phenyl | H | H | Cl | 2 | 0 |
| 35 | ethyl | ethyl | H | 2-propenyl | benzyl | H | H | Cl | 2 | 0 |
| 36 | ethyl | ethyl | H | 3-ethylphenyl | ethyl | H | H | Cl | 2 | 0 |
| 37 | ethyl | ethyl | H | H | ethyl | 1-$CH_3$ | 2-$CH_3$ | Cl | 2 | 0 |
| 38 | ethyl | ethyl | H | 2-chloro-1-methylethyl | ethyl | 2-$CH_3$ | H | Cl | 2 | 0 |
| 39 | ethyl | ethyl | H | methylamino | ethyl | H | H | Cl | 2 | 0 |
| 40 | ethyl | methyl | H | cyclopropyl | ethyl | 2-$C_2H_5$ | H | Cl | 2 | 0 |
| 41 | ethyl | ethyl | H | cinnamyl | naphthyl | H | H | Cl | 2 | 0 |
| 42 | i-propyl | i-propyl | H | propyl | tolyl | H | H | Cl | 2 | 0 |
| 43 | t-butyl | chloro | H | methyl | ethyl | H | H | Cl | 1 | 0 |
| 44 | methyl | bromo | H | ethyl | ethyl | H | H | Br | 1 | 0 |
| 45 | methyl | bromo | 3-methyl | propyl | propyl | H | H | Br | 1 | 1 |
| 46 | ethyl | iodo | 5-ethyl | ethyl | ethyl | H | H | I | 1 | 1 |
| 47 | t-butyl | t-butyl | H | t-butyl | t-butyl | H | H | I | 1 | 0 |
| 48 | methyl | fluoro | H | methyl | ethyl | H | H | Cl | 1 | 0 |
| 49 | ethyl | ethyl | H | amino | ethyl | H | H | Cl | 1 | 0 |
| 50 | ethyl | ethyl | H | dimethylamino | ethyl | H | H | Cl | 1 | 0 |
| 51 | ethyl | ethyl | H | N-ethyl-N-phenyl | ethyl | H | H | Cl | 1 | 0 |
| 52 | methyl | methyl | 4-nitro | methyl | ethyl | H | H | Br | 1 | 0 |
| 53 | methyl | methyl | 3-chlorine | methyl | ethyl | H | H | Cl | 1 | 1 |
| 54 | methyl | methyl | 4-bromo | methyl | ethyl | H | H | Br | 1 | 1 |
| 55 | t-butyl | methoxy | 4-methoxy | propyl | propyl | H | H | Cl | 1 | 1 |
| 56 | t-butyl | methoxy | H | ethynyl | ethyl | H | H | Br | 1 | 0 |
| 57 | ethyl | methyl | H | 2-oxopropyl | ethyl | H | H | Br | 1 | 0 |
| 58 | ethyl | methyl | 4-nitro | hydroxy-ethyl | methyl | H | H | Br | 1 | 0 |
| 59 | ethyl | ethyl | H | methoxy-methoxy | ethyl | H | H | Cl | 1 | 0 |
| 60 | ethyl | ethyl | H | 2-chloroallyl | ethyl | H | H | Cl | 1 | 0 |
| 61 | t-butyl | bromo | H | 2-propargyl | ethyl | H | H | Br | 1 | 0 |
| 62 | ethyl | ethyl | H | methyl | ethyl | H | H | Cl | 3 | 0 |
| 63 | ethyl | ethyl | H | methyl | ethyl | H | H | Cl | 3 | 0 |
| 64 | methyl | methyl | H | methyl | methyl | 2-methyl | 3-propyl | Cl | 3 | 0 |
| 65 | methyl | methyl | H | methyl | methyl | 2-isopropyl | H | Cl | 3 | 0 |
| 66 | methyl | methyl | H | methyl | methyl | H | H | Cl | 4 | 0 |

In order to illustrate the advantage of the present invention, the selective preemergence herbicidal activity of the preferred species of this invention, i.e., the compound of Example 1, representative of N-hydrocarbyloxyoxalyl-2-haloacetanilides, was determined in greenhouse tests on sugarbeets and selected weed plants, viz., wild oats, barnyardgrass, crabgrass, blackgrass and yellow foxtail.

In the procedure used in these tests, Ray silt loam top soil is mixed with about 0.05% by weight of krillium and sifted through a 12.7 mm screen. Prior to use, the prepared soil is fumigated with methyl bromide. After preparation, the Ray silt loam soil is placed in plastic pots to fill the pots and then compacted to a depth of 12.7 mm from the top of the pots. The pots are then seeded with the seeds of the plants under test. The seeds are then covered with a 12.7 mm layer of Ray silt loam. The herbicide, dissolved or suspended in acetone or other suitable solvent, is applied to the cover layer with a belt sprayer adjusted to deliver a dosage equivalent to 187 l/ha. Immediately after applying the herbicide, a 6.4 mm layer of water is applied to the surface of the soil in the pots. The pots are then placed in a greenhouse on a sand covered bench and watered by subirrigation as needed. Three weeks after application of the test chemical, the results are observed and recorded as percent inhibition of each species tested.

Following the above procedure, the compound of Example 1, viz., 2-chloro-N-($N^1$-ethoxyoxalyl acetamidomethyl)-2',6'-diethylacetanilide was tested at application rates of from 2.24 kg/ha down to 0.07 kg/ha against selected weeds in sugarbeets; the results are summarized in Tables 1A and 1B.

In Table 1A herbicidal preemergence activity data is shown for the compound of Example 1 in surgarbeets at application rates ranging from 2.24 kg/ha down to 0.07 kg/ha. Results are presented in Table 1B in terms of $GR_{15}$ and $GR_{85}$ rates and selectivity factors. "$GR_{15}$" is defined to mean the amount of herbicide required to produce a 15% growth reduction or inhibition in the crop plant, whereas "$GR_{85}$" is defned to mean the amount of herbicide required to produce an 85% growth reduction, injury or inhibition of the weed plants. The selectivity factor is calculated as the $GR_{15}/GR_{85}$ ratio, i.e., $GR_{15}$ for the crop divided by $GR_{85}$ for the weed, both rates in kg/ha. The selectivity factor is a guide to the effectiveness of a chemical as a selective herbicide. In Table 1B, the selectivity factor is shown in parenthesis.

mixed with 0.05% krillium in aluminum containers and compacted to 9.5 mm below the top edge of the container. Sufficient quantities of soil to provide a 9.5 mm cover layer for the planted seeds or propagules are treated with the appropriate quantity of the herbicidal

TABLE 1A

Preemergence Activity of Compound of Example 1 on Sugarbeets and Grass Weeds
(Percent Inhibition; Average of 2 Replications)

| Rate Kg/Ha | PLANT | | | | | |
|---|---|---|---|---|---|---|
| | Sugarbeets | Wild Oats | Barnyard Grass | L. Crab Grass | Black Grass | Yellow Foxtail |
| 2.24 | 10 | 95 | 100 | 95 | 95 | 100 |
| 1.12 | 0 | 85 | 100 | 85 | 90 | 100 |
| 0.56 | 0 | 75 | 95 | 65 | 85 | 100 |
| 0.28 | 0 | 55 | 95 | 20 | 50 | 100 |
| 0.14 | 0 | 40 | 95 | 10 | 30 | 85 |
| 0.07 | 0 | 20 | 90 | 0 | 0 | 60 |

TABLE 1B

Preemergence Activity of compound of Example 1 in Sugarbeets and Grass Weeds

| $GR_{15}$ Sugarbeets | $GR_{85}$ Wild Oats | $GR_{85}$ Barnyard Grass | $GR_{85}$ Crabgrass | $GR_{85}$ Black Grass | $GR_{85}$ Yellow Foxtail |
|---|---|---|---|---|---|
| >2.24 | 1.12 (>2.0) | <0.07 (>33.3) | 1.12 (>2.00) | 0.56 (>4.0) | 0.14 (>16.0) |

Referring to the data in Table 1A, it will be seen that the compound of Example 1 may be safely used on sugarbeets at a rate somewhat greater than 2.24 kg/ha, while still providing varying degrees of control at decreasing rates for the several weed species, ranging down to complete control of barnyard grass at rates below 0.07 kg/ha of the compound of Example 1.

It will be seen from the data in Table 1B that the compound of Example 1 achieved selective control of all five grass species in the presence of sugarbeets. The extent of control was greater than a 2 fold selectivity with respect to wild oats and crabgrass over 4 fold selectivity with respect to blackgrass, over 16 fold selectivity with respect to yellow foxtail and greater than 33.3 fold selectivity with respect to barnyard grass.

In yet another series of tests, the compound of Example 1 was tested on additional and different crop and weed plants; data from these tests is presented in Table 2. In these tests, the seeds or vegetative propagules of the plants to be tested are planted in Ray silt loam soil compound dissolved or suspended in acetone or other suitable solvent and the soil/herbicide mixture thoroughly blended. The treated soil containing the herbicide incorporated therein is then uniformly distributed as a 9.5 mm cover layer over the planted seeds or propagules. The pans are then placed in a greenhouse on benches containing a layer of coarse sand and watered by subirrigation as needed.

Approximately two weeks after initiation of the tests, the results are observed and recorded. A herbicide rating code is used to signify the extent of inhibition of each species in each pan as follows:

0 = less than 25% inhibition
1 = 25 to less than 50% inhibition
2 = 50 to less than 75% inhibition
3 = 75 to less than 100% inhibition
4 = 100% inhibition (complete kill)

In Table 2 a dash (-) indicates that the indicated plant was not present in the test for treatment at the specified rate.

TABLE 2

Preemergence Herbicidal Activity

| Rate Kg/Ha | Soybean | Sugar-beet | Wheat | Rice | Sorghum | Cocklebur | Wild Buck-wheat | Morning Glory | Hemp Sesbania | Lambs-quarters | Smart-weed | Velvet Leaf | Downy Brome | Panicum Spp. | Barnyard Grass | Crab-grass | Canada Thistle | Nutsedge | Quack-grass | Johnson-grass |
|---|---|---|---|---|---|---|---|---|---|---|---|---|---|---|---|---|---|---|---|---|
| 5.6 | 1 | 0 | 3 | 3 | 3 | 1 | 0 | 1 | 0 | 2 | 1 | 1 | 3 | 3 | 3 | 3 | 0 | 3 | 3 | 1 |
| 1.12 | 0 | 0 | 0 | 1 | 0 | 0 | 0 | 0 | 0 | 1 | 0 | 0 | 0 | 1 | 3 | 3 | — | — | — | — |
| 0.28 | 0 | 0 | 0 | 0 | 0 | 0 | 0 | 0 | 0 | 0 | 1 | 0 | 0 | 0 | 3 | 1 | — | — | — | — |
| 0.06 | 0 | 0 | 0 | 1 | 0 | 0 | 0 | 0 | 0 | 0 | 0 | 0 | 0 | 0 | 2 | 0 | — | — | — | — |

The data set forth in the foregoing tables clearly illustrate the efficacy of the preferred compound representative of the present invention as a selective herbicide useful in the control of undesirable weeds in the presence of such agricultrual crops as sugarbeets, soybeans, wheat, sorghum and rice.

The herbicidal compositions of this invention including concentrates which require dilution prior to application contain at least one active ingredient and an adjuvant in liquid or solid form. The compositions are prepared by admixing the active ingredient with an adjuvant including diluents, extenders, carriers and conditioning agents to provide compositions in the form of finely-divided particulate solids, granules, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these.

The compositions of this invention, particularly liquids and wettable powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isethionate, esters of sodium sulfosuccinate, sulfated or sulfonated fatty acid esters petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl, naphthalene sulfonates, sodium naphthalene sulfonate, and polymethylene bis-naphthalenesulfonate.

Wettable powders are water-dispersible compositions containing one or more active ingredients, a inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from about 5 to 95 parts of active ingredient, from about 0.25 to 25 parts of wetting agent, from about 0.25 to 25 parts of dispersant and from 4.5 to about 94.5 parts of inert solid extender, all parts being by weight of the total composition. Where required, from about 0.1 to 2.0 parts of the solid inert extender can be replaced by a corrosion inhibitor of anti-foaming agent or both.

Aqueous suspensions can be prepared by mixing together and grinding an aqueous slurry of water-insoluble active ingredient in the presence of dispersing agents to obtain a concentrated slurry of very finely-divided particles. The resulting concentrated aqueous suspension is characterized by its extremely small particle size, so that when diluted and sprayed, coverage is very uniform.

Emulsifiable oils are usually solutions of active ingredient in water-immiscible or partially water-immiscible solvents together with a surface active agent. Suitable solvents for the active ingredient of this invention include hydyrocarbons and water-immiscible ethers, esters or ketones. The emulsifiable oil compositions generally contain from about 5 to 95 parts active ingredient, about 1 to 50 parts surface active agent and about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate, a surface active agent such as those listed hereinbefore can be present in the composition. Natrual clays, pyrophyllites, illite and vermiculite are examples of operable classes of particulate mineral extenders. The preferred extenders are the porous, absorptive, preformed particles such as preformed and screened particulate attapulgite or heat expanded, particulate vermiculite, and the finely-divided clays such as kaolin clays, hydrated attapulgite or bentonitic clays. These extenders are sprayed or blended with the active ingredient to form the herbicidal granules.

The granular compositions of this invention generally contain from about 5 parts to about 30 parts by weight of active ingredient per 100 parts by weight of clay and 0 to about 5 parts by weight of surface active agent per 100 parts by weight of particulate clay. The preferred granular compositions contain from about 10 parts to about 25 parts by weight of active ingredient per 100 parts by weight of clay.

The compositions of this invention can also contain other additaments, for example, fertilizers, herbicides, other pesticides and the like used as adjuvants or in combination with any of the above-described adjuvants. Chemicals useful in combination with the active ingredients of this invention include, for example, triazines, ureas, carbamates, acetamides, acetanilides, uracils, acetic acids, phenols, thiolcarbamates, triazoles, benzoic acids, nitriles and the like such as:

3-amino-2,5-dichlorobenzoic acid
3-amino-1,2,4-triazole
2-methoxy-4-ethylamino-6-isopropylamino-s-triazine
2-chloro-4-ethylamino-6-isopropylamino-s-triazine
2-chloro-N,N-diallylacetamide
2-chloroallyl diethyldithiocarbamate
N'-(4-chlorophenoxy) phenyl-N,N-dimethylurea
1,1'-dimethyl-4,4-bipyridinium dichloride
isopropyl N-(3-chlorophenyl) carbamate
2,2-dichloropropionic acid
S-2,3-dichloroallyl N,N-diisopropylthiolcarbamate
2-methoxy-3,6-dichlorobenzoic acid
2,6-dichlorobenzonitrile
N,N-dimethyl-2,2-diphenylacetamide
6,7-dihydrodipyrido(1,2-a:2',1'-c)-pyrazidiinium salt
3-(3,4-dichlorophenyl)-1,1-dimethylurea
4,6-dinitro-o-sec-butylphenol
2-methyl-4,6L -dinitrophenol
ethyl N,N-dipropylthiolcarbamate
2,3,6-trichlorophenylacetic acid
5-bromo-3-isopropyl-6L -methyluracil
3-(3,4-dichlorophenyl)-1-methoxy-1-methylurea
2-methyl-4-chlorophenoxyacetic acid
3-(p-chlorophenyl)-1,1-dimethylurea
1-butyl-3-(3,4-dichlorophenyl)-1-methylurea N-1-naphthylphthalamic acid
1,1'-dimethyl-4,4'-bipyridinium salt
2-chloro-4,6-bis(isopropylamino)-s-triazine
2-chloro-4,6-bis(ethylamino)-s-triazine
2,4-dichlorophenyl-4-nitrophenyl ether
alpha, alpha, alpha-trifluoro-2,6-dinitro-N,N-dipropyl-p-toluidine
S-propyl dipropylthiolcarbamate
2,4-dichlorophenoxyacetic acid
N-isopropyl-2-chloroacetanilide
2',6'-diethyl-N-methoxymethyl-2-chloroacetanilide
monosodium acid methanearsonate
disodium methanearsonate
N-(1,1-dimethylpropynyl)-3,5-dichlorobenzamide Fertilizers useful in combination with the active ingredients include for example ammonium nitrate, urea, potash, and superphosphate. Other useful additaments include materials in which plant organisms take root and grow such as compost, manure, humus, sand and the like.

When operating in accordance with the present invention, effective amounts of the acetanilides are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds of this invention to the plant is essential and critical for the practice of the present invention. The exact amount of active ingredient to be employed is dependent upon various factors, including the plant species and stage of development thereof, the type and condition of soil, the amount of rainfall and the specific acetanilide employed. In selective preemergence application to the plants or to the soil a dosage of from 0.02 to about 11.2 kg/ha, preferably from about 0.04 to about 5.60 kg/ha of acetanilide is usually employed. Lower or higher rates may be required in some instances. One skilled in the art can readily determine from this specification, including the examples, the optimum rate to be applied in any particular case.

The term "soil" is employed in its broadest sense to be inclusive of all conventional "soils" as defined in Webster's New International Dictionary, Second Edition, Unabridged (1961). Thus the term refers to any substance or media in which vegetation may take root and grow, and includes not only earth but also compost, manure, muck, humus, sand and the like, adapted to support plant growth.

Although the invention is described with respect to specific modifications, the details thereof are not to be construed as limitations except to the extent indicated in the following claims.

What is claimed is:

1. A compound of the formula

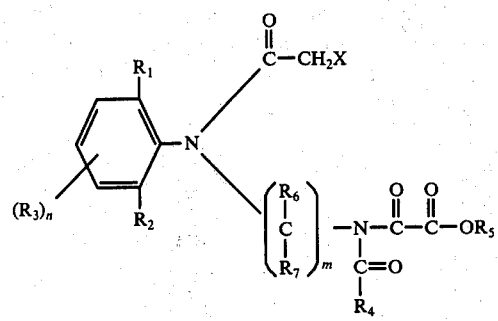

wherein
$R_1$ and $R_2$ are independently hydrogen, halogen, $C_{1-10}$ alkyl or alkoxy and may be the same or different;
$R_3$ is independently halogen, $C_{1-10}$ alkyl or alkoxy or $NO_2$ and when $n$ is 2 or 3 these groups may be the same or different;
$R_4$ is hydrogen, alkyl, alkenyl, alkynyl, alkoxyalkyl, polyalkoxyalkyl, haloalkyl, hydroxyalkyl, haloalkenyl, oxoalkyl, alkenyloxyalkyl, each of a maximum of 18 carbon atoms; $C_{3-6}$ cycloalkyl; aryl, alkaryl, aralkyl, or aryloxyalkyl, each of which may be substituted with halogen, alkyl and/or nitro groups and having at least 6 and not more than 24 carbon atoms; amino or mono- and dialkylamino, monoarylamino, mono(haloaryl)amino, mono(trifluoromethylaryl)amino, and alkylalkoxyamino having a maximum of 10 carbon atoms;
$R_5$ is alkyl, alkenyl, aryl, aralkyl or alkaryl having a maximum of 18 carbon atoms;
$R_6$ and $R_7$ are indenpendently hydrogen or $C_{1-4}$ alkyl and may be the same or different;
X is chlorine, bromine or iodine;
m i an integer of 1 to 4 inclusive and n is an integer of 0 to 3 inclusive.

2. Compound of claim 1 wherein $R_1$, $R_2$, $R_4$ and $R_5$ are $C_{1-10}$ alkyl.

3. Compound of claim 1 wherein $R_1$ is lower alkyl and $R_2$ is halogen.

4. Compound of claim 2 which is 2-chloro-N-($N^1$-ethoxyoxalyl acetamidomethyl)-2',6'-diethylacetanilide.

5. Compound of claim 3 which is 2-chloro-N-($N^2$-ethoxyoxalyl acetamidomethyl-2'-t-butyl-6'-chloroacetanilide.

6. A herbicidal composition comprising an adjuvant nd an effective amount of a compound of the formula

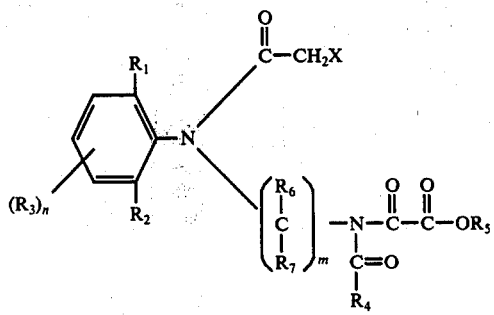

wherein
$R_1$ and $R_2$ are independently hydrogen, halogen, $C_{1-10}$ alkyl or alkoxy and may be the same or different;

$R_3$ is independently halogen, $C_{1-10}$ alkyl or alkoxy or $NO_2$ and when $n;l$ is 2 or 3 these groups may be the same or different;

$R_4$ is hydrogen, alkyl, alkenyl, alkynyl, alkoxyalkyl, polyalkoxyalkyl, haloalkyl, hydroxyalkyl, haloalkenyl, oxoalkyl, alkenyloxyalkyl, each of a maximum of 18 carbon atoms; $C_{3-6}$ cycloalkyl; aryl, alkaryl, aralkyl, or aryloxyalkyl, each of which may be substituted with halogen, alkyl and/or nitro groups and having at least 6 and not more than 24 carbon atoms; amino or mono- and dialkylamino, monoarylamino, mono(haloaryl)amino, mono(trifluoromethylaryl)amino, and alkylalkoxyamino having a maximum of 10 carbon atoms;

$R_5$ is alkyl, alkenyl, aryl, aralkyl or alkaryl having a maximum of 18 carbon atoms;

$R_6$ and $R_7$ are independently hydrogen or $C_{1-4}$ and may be the same or different;

X is chlorine, bromine or iodine, $m$ is an integer of 1 to 4 inclusive, and $n$ is an integer of 0 to 3 inclusive.

7. Composition of claim 6 wherein $R_1$, $R_2$, $R_4$, and $R_5$ are $C_{1-10}$ alkyl.

8. Composition of claim 6 wherein $R_1$ is lower alkyl and $R_2$ is halogen.

9. Composition of claim 7 wherein said compound is 2-chloro-N-(N¹-ethoxyoxalyl acetamidomethyl)-2',6'-diethylacetanilide.

10. Composition of claim 8 wherein said compound is 2-chloro-N-(N-ethoxyoxalyl acetamidomethyl)-2'-t-butyl-6'-chloroacetanilide.

11. A method for controlling undesirable vegetation which comprises applying to the locus thereof a herbicidal composition comprising an adjuvant and an effective amount of a compound of the formula

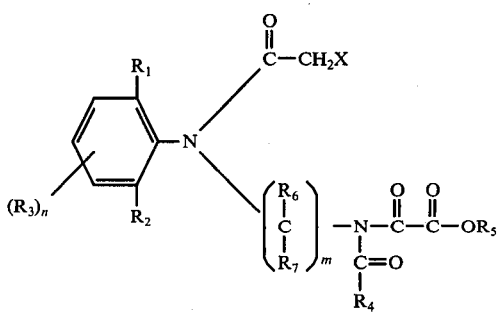

wherein $R_1$ and $R_2$ are independently hydrogen, halogen, $C_{1-10}$ alkyl or alkoxy and may be the same or different;

$R_3$ is independently halogen, $C_{1-10}$ alkyl or alkoxy or $NO_2$ and when $n$ is 2 or 3 these groups may be the same or different;

$R_4$ is hydrogen, alkyl, alkenyl, alkynyl, alkoxyalkyl, polyalkoxyalkyl, haloalkyl, hydroxyalkyl, haloalkenyl, oxoalkyl, alkenyloxyalkyl, each of a maximum of 18 carbon atoms; $C_{3-6}$ cycloalkyl; aryl, alkaryl, aralkyl, or aryloxyalkyl, each of which may be substituted with halogen alkyl and/or nitro groups and having at least 6 and not more than 24 carbon atoms; amino or mono- and dialkylamino, monoarylamino, mono(haloaryl)amino, mono(trifluoromethylaryl)amino, and alkylalkoxyamino having a maximum of 10 carbon atoms;

$R_5$ is alkyl, alkenyl, aryl, aralkyl or alkaryl having a maximum of 18 carbon atoms;

$R_6$ and $R_7$ are independently hydrogen or $C_{1-4}$ alkyl and may be the same or different;

X is chlorine, bromine or iodine, $m$ is an integer of 1 to 4 inclusive and $n$ is an integer of 0 to 3 inclusive.

12. Method of claim 11 wherein $R_1$, $R_2$, $R_4$, and $R_5$ are $C_{1-10}$ alkyl.

13. Method of claim 11 wherein $R_1$ is lower alkyl and $R_2$ is halogen.

14. Method of claim 12 wherein said compound is 2-chloro-N-(N¹-ethoxyoxalyl acetamidomethyl)-2',6'-diethylacetanilide.

15. Method of claim 13 wherein said compound is 2-chloro-N-(N¹-ethoxyoxalyl acetamidomethyl)-2'-t-butyl-6'-chloroacetanilide.

16. Method for the selective control of grass weeds in sugarbeets which comprises applying 2-chloro-N-(N¹-ethoxyoxalyl acetamidomethyl)-2',6'-diethylacetanilide.

* * * * *

UNITED STATES PATENT AND TRADEMARK OFFICE
CERTIFICATE OF CORRECTION

PATENT NO. : 4,055,414
DATED : October 25, 1977
INVENTOR(S) : John P. Chupp

It is certified that error appears in the above-identified patent and that said Letters Patent are hereby corrected as shown below:

Column 1, line 29, "amidoalkyl- b 2-" should read -- amidoalkyl-2- --.

Column 4, line 9, "13.6 L" should read -- 13.6 --.

At the following places in the claims "alkoxy....polyalkoxyalkyl" should be deleted:

Claim 1, Column 14, lines 21 and 22
Claim 6, Column 15, lines 4 and 5
Claim 11, Column 16, lines 21 and 22

Column 14, line 47, Claim 5, "2-chloro-N($N^2$-" should read -- 2-chloro-N($N^1$- --.

Column 14, line 47, "2-chloro-N-($N^2$-" should read -- 2-chloro-N-($N^1$- --.

Column 15, line 44, Claim 10 "2-chloro-N-ethoxyoxalyl" should read -- 2-chloro-N-($N^1$-ethoxyoxalyl --.

Signed and Sealed this

Sixteenth Day of May 1978

[SEAL]

Attest:

RUTH C. MASON
Attesting Officer

LUTRELLE F. PARKER
Acting Commissioner of Patents and Trademarks